(12) United States Patent
Reeve

(10) Patent No.: US 6,335,187 B1
(45) Date of Patent: Jan. 1, 2002

(54) RESOLUTION OF CHIRAL AMINES

(75) Inventor: Christopher David Reeve, Billingham (GB)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 09/555,924

(22) PCT Filed: Dec. 9, 1998

(86) PCT No.: PCT/GB98/03679

§ 371 Date: Jun. 6, 2000

§ 102(e) Date: Jun. 6, 2000

(87) PCT Pub. No.: WO99/31264

PCT Pub. Date: Jun. 24, 1999

(30) Foreign Application Priority Data

Dec. 12, 1997 (GB) .................................................. 9726229

(51) Int. Cl.⁷ .............................. C12P 13/00; C12P 13/02
(52) U.S. Cl. ............................................ 435/128; 435/128
(58) Field of Search ..................................... 435/128, 129

(56) References Cited

FOREIGN PATENT DOCUMENTS

| | | |
|---|---|---|
| DE | 43 32 738 | 3/1995 |
| DE | 195 23 151 | 8/1996 |
| WO | WO 91/19002 | 12/1991 |

OTHER PUBLICATIONS

Hiroshi Kitaguchi et al: "Enzymatic resolution of racemic amines: Crucial role of the solvent." Journal of the American Chemical Society., vol. 111, 1989, pp. 3094–3095, XPP002096761 DC US cited in the application see the whole document.

*Primary Examiner*—Herbert J. Lilling
(74) *Attorney, Agent, or Firm*—Pillsbury Winthrop LLP

(57) ABSTRACT

Chiral amines are resolved by selectively reacting an enantiomer of the amine with an alkyl ester in the presence of an enantioselective lipase enzyme to produce an amide of that enantiomer and separating it from the unreacted enantiomer, the alkyl group of the ester being an isoalkyl group. Isobutyl and especially isopropyl groups are preferred.

17 Claims, No Drawings

RESOLUTION OF CHIRAL AMINES

This application is the national phase of international application PCT/C7B98/03769 filed Dec. 9, 1998 which designated the U.S.

THIS INVENTION relates to the resolution of chiral amines.

It is known for example from WO95/08636, Kitaguchi et al (J.Am. Chem. Soc., 1989, 111, 3094–3095), Gotor et al (J.Chem. Soc. Perkin Trans. 1, 1993, 2453–2456), Ohmer et al (Enzyme and Microbial Technology, 1996, 19, 328–331) and Sanchez et al (Tetrahedron Asymmetry, 1997, 8, 37–40) and Chiou et al, Bio-organic & Medicinal Chemistry Letters Vol. 7, No 4, pp 433–436 (1977 to resolve racemic amines by acylating one enantiomer by reaction with an alkyl ester in the presence of an enantioselective enzyme as catalyst However, the results obtained have in many cases been disappointing.

We have found that such reactions of attractive stereospecificity occur if the alkyl group of the ester is an isoalkyl group preferably an isopropyl group.

The invention therefore comprises a process of resolution of chiral amines which comprises selectively reacting one enantiomer of the amine with an alkyl ester in the presence of a enantioselective lipase enzyme to produce an amide of one enantiomer and separating it from an unreacted enantiomer optionally after further reaction charactersed in that the alkyl group of the ester is an isoalkyl group and preferably an isopropyl group. A lipase is an enzyme capable of catalysing the esterification of aliphatic adds with glycerol and the hydrolysis of esters of glycerol and aliphatic adds.

Either or both enantiomers may be recovered. The untreated enantiomer may be recovered as such. The reacted enantiomer may be converted to the original amine enantiomer suitably by hydrolysis. It may of course be utilised as the amide if desired. Suitably such hydrolysis may be carried out using as catalyst an amidase of the same stereospecificity and/or hydrolysing any unwanted stereoisomer present using an amidase of opposite stereospecificity, separating the unwanted amide and hydrolysing that, thus providing a second stage of resolution and enhancing the enantiomeric excess of the product, but if the first stage provides sufficient specificity a non selective hydrolysis may be employed.

The acid component of the ester may have 1 to 10 for example 1 to 5 carbon atoms. It is preferably of formula RCOOH in which R is a hydrocarbyl group, for example an aryl group such as a phenyl, naphthyl or benzyl group, an alkyl or cydoalkyl group or a chloroor bromo substituted derivative thereof, the substitution being preferably on a carbon atom adjacent to the C=O group or one next to it It may suitably be an unsubstituted alkyl group suitably having 1 to 4 carbon atoms as these are often of moderate cost tend not to be involved in unwanted side reactions and tend not to be aggressive to metal reaction vessels.

The process is suitable for the resolution of primary and secondary amines for example amines of formula

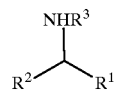

in which $R^1$ and $R^2$ are alkyl, cycloalkyl, alkenyl or alkynyl, or an aryl group or such a group, which is substituted with for example $NO_2$, $SO_3H$, $COOR^4$, Cl, Br, F, I, OH, SO, $SO_2$, CN, alkoxy and in the case of aryl substitution $NH_2$ in which $R^1$ and $R^2$ are different and $R^3$ is H, alkyl, cycloalkyl, alkenyl, alkynyl, or an aryl group or such a group which is substituted with for example, $NO_2$, $SO_3H$, COOH, Cl, Br, F, I, OH, SO, $SO_2$, CN and $R^4$ is alkyl, cycloalkyl, alkenyl, alkynyl or an aryl group optionally substituted as described above. The process is suitable for the resolution of amino acids and their esters.

The amine preferably has the formula

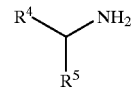

in which $R^4$ is an alkyl group having for example1 to 12 and preferably 1 to 6 carbon atoms and $R^5$ is an aryl preferably a naphthyl group, an alkyl group or cycloalkyl group in each case optionally substituted by one or more alkoxy, hydroxy, halogen and/or —CN group or in the case of aryl groups, amine groups, groups which preferably have at most 12 and more preferably at most 6 carbon atoms in total in all of the said substituents.

The amount of lipase present is preferably 10 to 50% by weight of the amine. The lipase is preferably supported on a solid support to enable it to be removed mechanically, for example by filtration or centrifugation, after reaction.

Separation of the amide of the reacted amine from unreacted amine may be accomplished by known methods, for example, distillation or crystallisation.

The reaction may be carried out in the presence of a solvent which may be the ester, an ether (for example methyl tert butyl ether, dimethoxy ethane or tetrahydrofuran) or a hydrocarbon, for example toluene or an alkane or cycloalkane having 5 to 10 carbon atoms or a halogenated hydrocarbon solvent. It is preferably free from —OH and $NH_2$ groups.

The reaction may be carried out at 20–60° C. for example at 20–40° C. At least one mole of the ester should be provided per two moles of the amine so as to permit stoichiometric reaction of an enantiomer, but it is preferred that an excess be provided. The excess should normally be sufficient to provide preferably at least 90% and more preferably at least 95% for example 99% reaction of the most reactive enantiomer. In judging the appropriate excess, conditions should not be such as to cause unacceptable conversion of the less reactive enantiomer, and if a very high selectivity for the more reactive enantiomer is needed it may be preferred to convert only part thereof, thus requiring little or no excess; indeed operation with less than the stoichiometrc amount may be desirable in some cases.

The step of converting the amine to the amide is preferably carried out in the substantial absence of water and other hydroxy compounds.

EXAMPLE 1

2-Amino-3, 3-dimethylbutane (125 mg) was added to 3 ml of acyl donor (e.g. ethyl acetate or isopropyl acetate) and incubated at 28° C. in the presence of 60 mg of immobilised lipase from *Candida antarctica* (NOVO SP 435). The extent of reaction was followed by quantitative gas chromatography on a Perkin Elmer 8500 system fitted with a J&W 30 m×0.32 mm fused silica capilliary GC The gas chromatograph was operated with helium carrier gas at 5.5×104 Pa (8 psi) using a temperature gradient starting at 80° C. and rising to 200° C. at a rate of 20° min⁻¹ followed by 6 minutes held at 200° C. Under such conditions 2-amino-3, 3-dimethylbutane was eluted with a retention time of 3.0 minutes and the corresponding acetamide at 6.1 minutes.

The enantiomeric purity of unreacted 2-amino-3, dimethylbutane (derivatised as the N-butyramide) and the acetamide product of the aminolysis reaction was determined by chiral phase gas chromatography using a 25 m×0.32 mm Chrompack CP-Chirasil-Dex CB column. The gas chromatograph was operated with a helium carrier gas at 5.5× 104 Pa (8 psi) and at 20° C. Under such conditions the two enantiomers of the acetamide derivative of 2-amino-3, 3-dimethylbutane were eluted with retention times of 4.78 minutes (S) and 4.95 minutes (R) and the two enantiomers of the butyramide derivative 8.38 minutes (S) and 8.51 minutes (R). The results are summarised in Table 1.

TABLE 1

Effect of structural changes to the alcohol component of the acyl donor on the enantioselectivity of the resolution of 2-amino-3,3-dimethylbutane by *Candida antarctica* lipase.

| Acyl donor | Reaction time (h) | Conversion (%) | E.e. unreacted amine (as butyramide) (%) | E.e. product (%) | Enantiomeric ratio (E) |
|---|---|---|---|---|---|
| Ethyl acetate | 216 | 39.2 | 50 | 78 | 13 |
| Isopropyl acetate | 216 | 46.5 | 83 | 95 | 104 |

EXAMPLE 2

1-(1-Naphthyl) ethylamine (100 mg) was added to 5 ml of acyl donor e.g. ethyl acetate or isopropyl acetate) and incubated at 28° C. in the presence of 50 mg of immobilised *Candida antarctica* lipase (NOVO SP 435). The extent of conversion was determined from measurements of the enantiomeric excess of the unreacted amine (derivatised as its butyramide) and product acetamide using the mathematical expression described by Chen et. al. (J. Am. Chem. Soc., 1982, Vol 104, pp 7294–7299). Enantiomeric excess measurements were made by chiral phase HPLC on a Hewlett Packard HP 1050 system fitted with a 250 mm×4.6 mm Daicel Chiralcel OD column. The column was eluted isocratically with a mixture of 92.5% hexane and 7.5% ethanol in 1 ml min$^{-1}$. Compounds were detected by UV absorbance at 254 mm. The retention times of the unreacted amine (derivatised as its butyramide) were 7.65 minutes (R) and 15.2 minutes (S) and the product acetamide 8.9 minutes (R) and 17.9 minutes (S). The results are summarised in Table 2.

TABLE 2

Effect of structural changes to the alcohol component of the acyl donor on the enantioselectivity of the resolution of 1-(1-naphthyl) ethylamine by *Candida antarctica* lipase.

| Acyl donor | Reaction time (h) | Conversion (%) | E.e. unreacted amine (as butyramide) (%) | E.e. product (%) | Enantiomeric ratio (E) |
|---|---|---|---|---|---|
| Ethyl acetate | 70 | 52.5 | 66 | 60 | 8 |
| Isopropyl acetate | 66 | 48.9 | 88 | 92 | 70 |

EXAMPLE 3

Racemic 1-(1-naphthyl)ethylamine (100 mg) was added to 5 ml of acyl donor (see Table 3) and incubated at ambient temperature in the presence of 20 mg of Chirazyme L2 (immobilised *Candida antarctica* lipase). At intervals 0.5 ml samples were removed and diluted to 1 ml with a solution of hexanelethanol (92.5:7.5). The unreacted amine was converted to its corresponding butyramide by the addition of 10 μl of butyric anhydride. Each sample was analysed by chiral phase HPLC on a Hewlett Packard HP1050 system using a Daicel Chiralcel OD analytical column (250 mm×4.6 mm) eluted with hexanelethanol (92.5:7.5) at a flow rate of 1 ml min$^{-1}$. Compounds were detected by UV absorbance at 254nm. The retention times of the two enantiomers of the unreacted amine (derivatised as its butyramide) were 7.9 minutes (R) and 15.0 minutes (S) and the product acetamide 9.3 minutes (R) and 17.9 minutes (S). The extent of conversion and enantiomeric ratio was determined from measurements of the enantiomeric excess of unreacted amine and product acetamide using the mathematical expression described by Chen et. al. (J. Am. Chem. Soc., 1982, Vol 104, pp 7294–7299). The results are summarised in Table 3.

TABLE 3

Effect of structural changes to the alcohol component of the acyl donor on the enantiospecificity of the resolution of 1-(1-naphthyl)ethylamine by Chirazyme L2 lipase.

| Acyl donor | Time (h) | Conversion (%) | E.e. of unreacted amine (%) | E.e. of product acetamide (%) | Enantiomeric ratio (E) |
|---|---|---|---|---|---|
| Methyl acetate | 120 | 30 | 6 | 13 | 1 |
| Ethyl acetate | 120 | 43 | 59 | 79 | 15 |
| n-Propyl acetate | 120 | 40 | 54 | 81 | 16 |
| n-Butyl acetate | 120 | 32 | 40 | 77 | 18 |
| Isopropyl acetate | 72 | 45 | 78 | 95 | 100 |
| Isobutyl acetate | 72 | 50 | 86 | 88 | 37 |
| Isoamyl acetate | 72 | 44 | 68 | 88 | 28 |

EXAMPLE 4

Racemic 1,2,3,4-tetrahydro1-naphthylamine (100 mg) was added to 5 ml of acyl donor (see Table 4) and incubated at ambient temperature in the presence of 20 mg of Chirazyme L2 (immobilised *Candida antarctica* lipase). At intervals 0.5 ml samples were removed and diluted to 1 ml with dichloromethane. The unreacted amine was converted to its corresponding butyramide by the addition of 10 μl of butyric anhydride. Each sample was analysed by chiral phase GC on a Perkin Elmer 8700 system using a Chrompack CP-Chirasil-Dex CB column (25 m×0.32 mm). The gas chromatograph was operated isothermally at 175° C. with helium carrier gas at 5.5×104 Pa (8 psi) Compounds were detected by flame ionisation. The retention times of the two enantiomers of the unreacted amine (derivatised as its butyramide) were 23.8 minutes (S) and 25.8 minutes (R) and the product acetamide 14.4 minutes (S) and 15.9 minutes (R). The extent of conversion and enantiomeric ratio was determined from measurements of the enantiomeric excess of unreacted amine and product acetamide using the mathematical expression described by Chen et. al (J. Am. Chem. Soc., 1982, Vol 104, pp 7294–7299). The results are summarised in Table 4.

TABLE 4

Effect of structural changes to the alcohol component of the acyl donor on the enantiospecificity of the resolution of 1,2,3,4-tetrahydro-1-naphthylamine by Chirazyme L2 lipase.

| Acyl donor | Time (h) | Conversion (%) | E.e. of unreacted amine (%) | E.e. of product acetamide (%) | Enantiomeric ratio (E) |
|---|---|---|---|---|---|
| Methyl acetate | 72 | 57 | 16 | 12 | 1 |
| Ethyl acetate | 72 | 54 | 82 | 69 | 14 |
| n-Propyl acetate | 72 | 52 | 78 | 74 | 14 |
| n-Butyl acetate | 72 | 26 | 14 | 42 | 3 |
| Isopropyl acetate | 72 | 50 | 98 | 97 | 458 |
| Isobutyl acetate | 72 | 53 | 95 | 83 | 43 |
| Isoamyl acetate | 72 | 46 | 70 | 81 | 21 |

EXAMPLE 5

Racemic 2-amino3,3-dimethylbutane (100 mg) was added to 5 ml of acyl donor (see Table 5) and incubated at ambient temperature in the presence of 40 mg of Chirazyme L2 (immobilised *Candida antarctica* lipase). At intervals 0.5ml samples were removed and diluted to 1 ml with dichloromethane. The unreacted amine was converted to its corresponding butyramide by the addition of 10 μl of butyric anhydride. Each sample was analysed by chiral phase GC on a Perkin Elmer 8700 system using a Chrompack CP-Chirasil-Dex CB column (25 m×0.32 mm). The chromatograph was operated isothermally at 120° C. with helium carrier gas at 5.5×104 Pa (8 psi). Compounds were detected by flame ionisation. The retention times of the two enantiomers of the unreacted amine (derivatised as its butyramide) were 10.3 minutes (S) and 10.5 minutes (R) and the product acetamide 5.6 minutes (S) and 5.9 minutes (R). The extent of conversion and enantiomeric ratio was determined from measurements of the enantiomeric excess of unreacted amine and product acetamide using the mathematical expression described by Chen et al. (J. Am. Chem. Soc., 1982, Vol 104, pp 7294–7299). The results are summarised in Table 5.

TABLE 5

Effect of structural changes to the alcohol component of the acyl donor on the enantiospecificity of the resolution of 2-amino-3,3-dimethylbutane by Chirazyme L2 lipase.

| Acyl donor | Time (h) | Conversion (%) | E.e. of unreacted amine (%) | E.e. of product acetamide (%) | Enantiomeric ratio (E) |
|---|---|---|---|---|---|
| Methyl acetate | 168 | 29 | 2 | 5 | 1 |
| Ethyl acetate | 168 | 34 | 36 | 69 | 8 |
| n-Propyl acetate | 168 | 26 | 24 | 69 | 7 |
| n-Butyl acetate | 168 | 17 | 13 | 62 | 5 |
| Isopropyl acetate | 168 | 41 | 67 | 98 | 109 |
| Isobutyl acetate | 168 | 33 | 44 | 88 | 27 |
| Isoamyl acetate | 168 | 25 | 26 | 79 | 10 |

EXAMPLE 6

Racemic 1-(1-naphthyoethylamine (100 mg) was added to a solution of 4 ml of dimethoxyethane and 1 ml of acyl donor (see Table 6) and incubated at ambient temperature in the presence of 20 mg of Chirazyme L2 (immobilised *Candida antarctica* lipase). At intervals 0.5 ml samples were removed and diluted to 1 ml with a solution of hexaneletha-nol (92.5:7.5). The unreacted amine was converted to its corresponding butyramide by the addition of 10 μl of butyric anhydride. Each sample was analysed by chiral phase HPLC as described in Example 3. The results are summarised in Table 6.

TABLE 6

Effect of structural changes to the alcohol component of the acyl donor on the enantiospecificity of the resolution of 1-(1-naphthyl)ethylamine in dimethoxyethane by Chirazyme L2 lipase.

| Acyl donor | Time (h) | Conversion (%) | E.e. of unreacted amine (%) | E.e. of product acetamide (%) | Enantiomeric ratio (E) |
|---|---|---|---|---|---|
| Methyl acetate | 168 | 26 | 276 | 77 | 10 |
| Ethyl acetate | 168 | 37 | 53 | 91 | 33 |
| n-Propyl acetate | 168 | 34 | 47 | 92 | 35 |
| n-Butyl acetate | 168 | 36 | 52 | 94 | 43 |
| n-amyl acetate | 168 | 22 | 26 | 93 | 32 |
| Isopropyl acetate | 168 | 44 | 78 | >98 | 650 |
| Isobutyl acetate | 168 | 40 | 64 | 95 | 95 |
| Isoamyl acetate | 168 | 35 | 51 | 94 | 61 |

EXAMPLE 7

Racemic 1,2,3,4-tetrahydro-1-naphthylamine (100 mg) was added to a solution of 4 ml of dimethoxyethane and 1 ml of acyl donor (see Table 7) and incubated at ambient temperature in the presence of 20 mg of Chirayme L2 (ummobilised *Candida antarctica* lipase). At intervals 0.5 ml samples were removed and diluted to 1 ml with dichloromethane. The unreacted amine was converted to its corresponding butyramide by the addition of 10 μl of butyric anhydride. Each sample was analysed by chiral phase GC as described in Example 4. The results are summarised in Table 7.

TABLE 7

Effect of structural changes to the alcohol component of the acyl donor on the enantiospecificity of the resolution of 1,2,3,4-tetrahydro-1-naphthylamine in dimethoxyethane by Chirazyme L2 lipase.

| Acyl donor | Time (h) | Conversion (%) | E.e. of unreacted amine (%) | E.e. of product acetamide (%) | Enantiomeric ratio (E) |
|---|---|---|---|---|---|
| Methyl acetate | 120 | 41 | 49 | 69 | 9 |
| Ethyl acetate | 120 | 47 | 85 | 95 | 129 |
| n-Propyl acetate | 120 | 47 | 83 | 94 | 79 |
| n-Butyl acetate | 120 | 42 | 68 | 95 | 65 |
| n-Amyl acetate | 120 | 34 | 46 | 90 | 28 |
| Isopropyl acetate | 120 | 50 | 96 | 98 | 194 |
| Isobutyl acetate | 120 | 50 | 97 | 96 | 278 |
| Isoamyl acetate | 120 | 42 | 69 | 96 | 86 |

EXAMPLE 8

Racemic 2-amino-3,3-dimethylbutane (100 mg) was added to a solution of 4 ml of dimethoxyethane and 1 ml of acyl donor (see Table 8) and incubated at ambient temperature in the presence of 40 mg of Chirazyme L2 Cimmobilised *Candida antarctica* lipase). At intervals 0.5 ml samples were removed and diluted to 1 ml with dichloromethane. The unreacted amine was converted to its corresponding butyramide by the addition of 10 µl of butyric anhydride. Each sample was analysed by chiral phase GC as described in Example 5. The results are summansed in Table 8.

TABLE 8

Effect of structural changes to the alcohol component of the acyl donor on the enantiospecificity of the resolution of 2-amino-3,3-dimethylbutane in dimethoxyethane by Chirazyme L2 lipase.

| Acyl donor | Time (h) | Conversion (%) | E.e. of unreacted amine (%) | E.e. of product acetamide (%) | Enantiomeric ratio (E) |
|---|---|---|---|---|---|
| Methyl acetate | 336 | 22 | 17 | 59 | 5 |
| Ethyl acetate | 336 | 29 | 37 | 90 | 29 |
| n-Propyl acetate | 336 | 27 | 34 | 91 | 33 |
| n-Butyl acetate | 336 | 25 | 30 | 91 | 26 |
| n-Amyl acetate | 336 | 17 | 18 | 86 | 19 |
| Isopropyl acetate | 336 | 36 | 56 | >98 | 791 |
| Isobutyl acetate | 336 | 30 | 41 | 96 | 68 |
| Isoamyl acetate | 336 | 27 | 35 | 94 | 51 |

EXAMPLE 9

Racemic 1-(1-naphthyoethylamine (100 mg) was added to 5 ml of acyl donor (see Table 9) and incubated at ambient temperature in the presence of 50 mg of Chirazyme L6 (Pseudomonas species lipase). At intervals 0.2 ml samples were removed and diluted to 1 ml with a solution of hexaneIethanol (92.5:7.5). The unreacted amine was converted to its corresponding butyramide by the addition of 4 µl of butyric anhydride. Each sample was analysed by chiral phase HPLC as described in Example 3. The results are summarsed in Table 9.

TABLE 9

Effect of structural changes to the alcohol component of the acyl donor on the Enantiospecificity of the resolution of 1-(1-naphthyl)ethylamine by Chirazyme L6 lipase.

| Acyl donor | Time (h) | Conversion (%) | E.e. of unreacted amine (%) | E.e. of product acetamide (%) | Enantiomeric ratio (E) |
|---|---|---|---|---|---|
| Ethyl acetate | 266 | 21 | 12 | 47 | 3 |
| Isopropyl acetate | 266 | 12 | 12 | 87 | 18 |

EXAMPLE 10

Racemic 1,2,3,4-tetrahydro-1-naphthylamine (100 mg) was added to 5 ml of acyl donor (see Table 10) and incubated at ambient temperature in the presence of 50 mg of Chirazyme L6 (Pseudomonas species lipase). At intervals 0.2 ml samples were removed and diluted to 1 µl with MTBE. The unreacted amine was converted to its corresponding butyramide by the addition of 6 ml of butyric anhydride. Each sample was analysed by chiral phase GC as described in Example 4. The results are summarised in Table 10.

TABLE 10

Effect of structural changes to the alcohol component of the acyl donor on the Enantiospecificity of the resolution of 1,2,3,4-tetrahydro-1-naphthylamine by Chirazyme L6 lipase.

| Acyl donor | Time (h) | Conversion (%) | E.e. of unreacted amine (%) | E.e. of product acetamide (%) | Enantiomeric ratio (E) |
|---|---|---|---|---|---|
| Ethyl acetate | 244 | 43 | 18 | 24 | 2 |
| Isopropyl acetate | 244 | 36 | 50 | 90 | 28 |

Chirazyme is a trade mark of Boehringer Mannheim GmbH
Chiralcel is a trade mark of Daicel Chemical Industries Limited

What is claimed is:

1. A process of resolution of chiral amines which comprises selectively reacting an enantiomer of the amine with an alkyl ester in the presence of a enantioselective lipase enzyme to produce an amide of that enantiomer and separating it from an unreacted enantiomer optionally after further reaction characterised in that the acid component of the ester has 1 to 10 carbon atoms and the parent acid is of formula RCOOH in which R is a hydrocarbyl group and the alkyl group of the ester is an isoalkyl group.

2. A process as claimed in claim 1 in which the isoalkyl group is an isobutyl or isopropyl group.

3. A process as claimed in claim 1 or 2 in which the unreacted enantiomer is recovered as such.

4. A process as claimed in claims 1 or 2 in which the reacted enantiomer is converted to the original amine enantiomer by hydrolysis.

5. A process as claimed in claim 1 or 2 in which the reacted enantiomer is utilised in its amide form.

6. A process as claimed in claim 1 or claim 2 in which the hydrocarbyl group R is an unsubstituted alkyl group having 1 to 4 carbon atoms.

7. A process as claimed in claim 1 or claim 2 in which 10 to 50% by weight of lipase is present based on the amine.

8. A process as claimed in claim 1 or claim 2 in which the lipase is supported on a solid support.

9. A process as claimed in claim 1 or claim 2 which is carried out in the presence of a solvent which is an ester, ether or hydrocarbon or a halogenated hydrocarbon which is free from OH and $NH_2$ groups.

10. A process as claimed in claim 1 or claim 2 which is carried out at a temperature of 20 to 60° C.

11. A process as claimed in claim 1 or claim 2 in which the amine has the formula

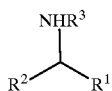

in which $R^1$ and $R^2$ are, independently, an alkyl, cycloalkyl, alkenyl, alkynyl, or aryl group, said group being unsubstituted or substituted with a substituent selected from the group consisting of $NO_2$, $SO_3H$, $COOR^4$, Cl, Br, F, I, OH, SO, $SO_2$, CN, alkoxy and, in the case of aryl groups, $NH_2$ in which $R^1$ and $R^2$ are different;

$R^3$ is H, an alkyl, cycloalkyl, alkenyl, alkynyl, or aryl group, said group being unsubstituted or substituted with a substituent selected from the group consisting of $NO_2$, $SO_3H$, $COOR^4$, Cl, Br, F, I, OH, SO, $SO_2$, CN and alkoxy; and $R^4$ is an alkyl, cycloalkyl, alkenyl, alkynyl or aryl group optionally substituted by one or more $NO_2$, $SO_3H$, $COOR^3$, Cl, Br, F, I, OH, SO, $SO_2$, CN or alkoxy groups.

12. A process as claimed in claim 11 in which the amine has the formula

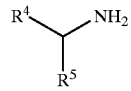

in which $R^4$ is an alkyl group having from 1 to 12 carbon atoms and $R^5$ is an aryl, alkyl or cycloalkyl group, $R^5$ being optionally substituted by one or more substituents selected from the group consisting of alkoxy, hydroxy, halogen, cyano, and when $R^5$ is aryl, amine groups.

13. A process according to claim 12 in which $R^4$ is an alkyl group having from 1 to 6 carbon atoms.

14. A process according to claim 12 in which $R^5$ is either unsubstituted or substituted by substituents having at most 6 carbons in total in all of the said substituents.

15. A process according to claim 12 in which the hydrocarbyl group R is an unsubstituted alkyl group having 1 to 4 carbon atoms.

16. A process according to claim 15 in which $R^5$ is unsubstituted.

17. A process according to claim 16 in which $R^4$ is an alkyl group having from 1 to 6 carbon atoms.

* * * * *